(12) United States Patent
Abonnenc et al.

(10) Patent No.: US 8,926,815 B2
(45) Date of Patent: Jan. 6, 2015

(54) METHOD FOR THE SELECTION AND/OR THE PROCESSING OF PARTICLES, IN PARTICULAR CELLS

(75) Inventors: Mélanie Abonnenc, Valence (FR); Nicoló Manaresi, Bologna (IT); Gianni Medoro, Casalecchio do Reno (IT)

(73) Assignee: Silicon Biosystems S.p.A, Bologna (IT)

( * ) Notice: Subject to any disclaimer, the term of this patent is extended or adjusted under 35 U.S.C. 154(b) by 1628 days.

(21) Appl. No.: 12/297,037

(22) PCT Filed: Apr. 13, 2007

(86) PCT No.: PCT/IB2007/000973
§ 371 (c)(1),
(2), (4) Date: Oct. 13, 2009

(87) PCT Pub. No.: WO2007/119154
PCT Pub. Date: Oct. 25, 2007

(65) Prior Publication Data
US 2010/0068780 A1 Mar. 18, 2010

(30) Foreign Application Priority Data
Apr. 13, 2006 (IT) .............................. TO2006A0278

(51) Int. Cl.
*B03C 5/00* (2006.01)
*B03C 5/02* (2006.01)

(52) U.S. Cl.
CPC ................. *B03C 5/005* (2013.01); *B03C 5/026* (2013.01)
USPC ..................... 204/547; 435/173.1; 435/173.4; 435/173.5; 435/173.6; 435/173.9

(58) Field of Classification Search
None
See application file for complete search history.

(56) References Cited

U.S. PATENT DOCUMENTS

| | | | |
|---|---|---|---|
| 4,246,344 A | 1/1981 | Silver, III | |
| 6,027,488 A * | 2/2000 | Hofmann et al. | 604/522 |
| 6,280,586 B1 | 8/2001 | Wolf et al. | |
| 6,294,063 B1 | 9/2001 | Becker et al. | |
| 6,448,794 B1 * | 9/2002 | Cheng et al. | 324/693 |
| 6,492,175 B1 * | 12/2002 | Muller et al. | 435/450 |
| 6,858,439 B1 | 2/2005 | Xu | |
| 2002/0036141 A1 | 3/2002 | Gascoyne | |
| 2003/0104588 A1 * | 6/2003 | Orwar et al. | 435/173.6 |
| 2003/0146100 A1 | 8/2003 | Huang et al. | |
| 2004/0191789 A1 * | 9/2004 | Manaresi et al. | 435/6 |
| 2004/0209354 A1 | 10/2004 | Mathies et al. | |
| 2004/0211669 A1 | 10/2004 | Cummings et al. | |
| 2004/0224397 A1 | 11/2004 | Culbertson et al. | |
| 2005/0070018 A1 | 3/2005 | Johnson et al. | |
| 2005/0072677 A1 * | 4/2005 | Gascoyne et al. | 204/547 |
| 2005/0120402 A1 | 6/2005 | St. John et al. | |
| 2005/0211559 A1 | 9/2005 | Kayyem | |

FOREIGN PATENT DOCUMENTS

| | | |
|---|---|---|
| JP | 2002536167 A | 8/2001 |
| JP | 2004503775 A | 12/2002 |
| WO | WO-0047322 | 8/2000 |
| WO | WO00/69565 | 11/2000 |
| WO | WO-0196857 | 12/2001 |
| WO | WO03/001193 | 1/2003 |
| WO | WO-03001193 A1 | 1/2003 |
| WO | WO03/014739 | 2/2003 |
| WO | WO2004/071668 | 8/2004 |
| WO | WO2005/075656 | 8/2005 |
| WO | WO2007/049103 | 5/2007 |
| WO | WO 2007079663 A1 * | 7/2007 |

OTHER PUBLICATIONS

Maswiwat, K et al. On the field distribution in electrorotation chambers—Influence of electrode shape. Electrochimica Acta. 2006. 51: 5215-5220. Published online May 3, 2006.*
Hughes, MP. Computer-aided analysis of conditions for optimizing practical electrorotation. Phys. Med. Biol. 1998. 43: 3639-3648.*
Lin, Y et al. Simulation and experimental demonstration of the electric field assisted electroporation microchip for in vitro gene delivery enhancement. Lab Chip. 2004. 4: 104-108.*
International Search Report for PCT/IB2007/000973 dated Sep. 28, 2007.
Cordero et al, Microelectronics Journal, vol. 34, pp. 1137-1142 (2003).
Lu et al., Lab Chip, vol. 5, pp. 23-29 (2005).
Office Action of JP2009-504847 Dated Aug. 21, 2012 With an English Translation.
Office Action of JP2009-504849 Dated Aug. 21, 2012 With an English Translation.

* cited by examiner

*Primary Examiner* — Allison Fox
*Assistant Examiner* — Susan E Fernandez
(74) *Attorney, Agent, or Firm* — Venable LLP; Robert Kinberg; F. Brock Riggs

(57) ABSTRACT

Method for the selection or the processing of first particles sensitive to the application of an external stimulus including the step of producing, through the application of the external stimulus, the permeabilization of at least a selected first particle, consisting in the organization of the first particles through a first force field, to generate a second force field substantially placed in proximity of at least a selected first particle to be permeabilized.

23 Claims, 2 Drawing Sheets

METHOD FOR THE SELECTION AND/OR THE PROCESSING OF PARTICLES, IN PARTICULAR CELLS

TECHNICAL FIELD

The present invention relates to a method for the selection and/or the processing of particles, in particular particles consisting of cells or including cells or cell material and finds its application mainly in the implementation of protocols with a resolution on a single cell. By cell "processing" is understood to mean, herein and below, any type of operations which can be carried out on a single particle or cell, or groups of the same.

STATE OF THE ART

PCT/WO 00/69565 patent to G. Medoro describes an apparatus and a method for the manipulation and the detection/recognition of particles through the use of closed dielectrophoretic potential cages and integrated sensors, if any. The method described teaches how to control the position of each particle independently of all the others in a two-dimensional space. The force used for trapping in suspension particles in a fluid medium is the negative dielectrophoresis. The single control on the manipulation operations takes place through the programming of memory elements and circuits associated with each element of an array of electrodes and sensors integrated within a same substrate. The device allows to isolate cells, but it requires the displacement of these towards a second microchamber, fluidically isolated from the first one. Furthermore, a method for transforming the cells is not foreseen.

U.S. Pat. No. 6,294,063 patent, Becker et al, describes a method and an apparatus for the manipulation of packages of solid, liquid or gaseous biological material, through a distribution of programmable forces. The patent also mentions the use of sensors. Also in this case the cell isolation can take place only by physically moving cells throughout the device.

A further force for the manipulation of particles is the viscous friction force generated by electro-hydrodynamic (EHD) flows, such as the electro-thermal flows (ETF) or the AC electroosmosis. In N G. Green, A. Ramos and H. Morgan, J. Phys. D: Appl. Phys. 33 (2000), EHDs are used for displacing particles. For example, PCT WO 2004/071668 A1 discloses an apparatus for concentrating particles on some electrodes, by exploiting the so-called electro-hydrodynamic flows.

In the Italian patent application BO2005A000481, Medoro et al., some methods for manipulating particles with arrays of electrodes and some methods and apparatus for their detection are reported. Further, in the international patent application no. PCT/IT02/00524, a method in which first biological entities can be transformed by contacting the same with second biological entities (for example DNA-containing liposomes, or microballs) is described, wherein first biological entities are immobilized on a surface defined by a matrix of first electrodes at least partly selectively activable and addressable, arranged faced towards at least a second electrode, and are contacted with the second biological entities displaced by means of dielectrophoresis cages.

PCT IB 2006000636 patent application of the same Applicant relates to a method and an apparatus for the characterization and/or the counting of particles through non uniform, time varying force fields and integrated optical or impedance meter sensors. Force fields can be of positive or negative dielectrophoresis, electrophoresis or electro-hydrodynamic motions, characterized by a set of stable points of equilibrium for the particles (solid, liquid or gaseous); the same method is suitable for the manipulation of droplets (liquid particles) by exploiting effects known as Electrowetting on dielectric, with the aim of acting on the control of the position each particle existing in the sample, for the purpose of displacing such particles in a deterministic or statistical way, in order to detect their presence with the integrated optical or impedance meter sensors and/or characterize their type, for the purpose of counting or manipulating them in an efficient way.

In the Italian application in the same applicant's name, no. TO2006A000226 dated 27, Mar. 2006, methods and apparatus for the processing (for example washing, incubation, etc.) of particles are described, wherein the suspending particles in a first fluid are introduced in a laminar flow regime in at least a first microchamber or first region of the same, wherein a second fluid is introduced in a laminar flow regime in at least a second region of the micro-chamber or a second microchamber, in such a way not to mix itself with the first fluid, and wherein within the micro-chamber/s at least a force field (F) acting on the particles is activated, in order to cause a displacement of the particles only in a pre-fixed direction and transfer the same in suspension in the second fluid; there is preferably used an apparatus including at least three microchambers arranged in sequence to one another along a direction, each one connected with the micro-chamber immediately preceding and following through two orifices staggered to each other in a direction perpendicular to the sequence direction of the micro-chambers.

Recently, in the article A single cell electroporation chip, *Lab on a Chip*, 2005, 5 (1), 38-43, Michelle Khine, Adrian Lau, Cristian Ionescu-Zanetti, Jeonggi Sec and Luke P. Lee it was described how to increment the permeability of cell membranes through electroporation carried out on single cells; in this way, polar substances which could not otherwise permeate the plasmatic membrane (such as dyes, drugs, DNA, proteins, peptides and amino acids) can be introduced within the cell.

The article Flow-through micro-electroporation chip for high efficiency single-cell genetic manipulation, Sensors and Actuators *A: Physical*. Volume 104, Issue 3, May 15, 2003, Pages 205-212, Yong Huang, Boris Rubinsky describes in particular the genetic manipulation of single cells, which is of a great interest in fields such as biology and biotechnologies, obtained through an electroporation chip which uses microfluidic channels for accurately manipulating single cells; as it is known, the electroporation is a technique which uses strong electric fields for inducing structural rearrangements in the cell membrane; pores are thus formed through the membrane when the trans-membrane potential overcomes the dielectric perforation voltage of the membrane (0.2-1.5V) allowing to external substances to penetrate the membrane and reach the cytoplasm contained therein.

Electroporation of single cells is a technique of interest also because it allows to study the variations occurring in a cell population cell by cell, as well as to study the intracellular chemistry, for example by providing specific phenotypes to single cells activating or blocking the expression of specific and single protein. Using a technology based on the use of matrixes implemented on chips it is therefore possible to carry out HTS (high throughput screening) test equipments correlated both to the DNA and protein expression, and to chemical compounds (for example drugs) which are directed towards specific cellular targets (for example receptors).

The electroporation of single cells is moreover an advantageous technology with respect to protocols of "in bulk" electroporation normally used, which require very high voltages (>103 V) and which do not allow an effective control of the permeability of single cells, so that, for example, the re-closure of previously opened pores results difficult.

Attempts carried out so far in order to attain the electroporation of single cells include the use of microelectrodes made of carbon fiber (Lundqvist at al., 1998) and other techniques, such as capillaries filled of electrolytes, micropipettes and micro-manufactured chips.

Micro-manufactured chips are ideal both for isolating single cells and for focusing the electric field.

Finally, the article "Controlling cell destruction using dielectrophoretic forces", A. Menachery and R. Pethig, *IEE Proc.-Nanobiotechnol.*, Vol. 152, No. 4, August 2005, reports a study on lysis of cells for different kinds of cells in castellated or polynomial electrodes, and proposes the lysis or the differential electroporation of cells of different kinds existing in a mixture (selecting such frequencies and amplitudes that lysis or electroporation of a type is performed, but another type is saved).

However, as the electrodes are much greater than cells, the use of this approach is not proposed, and probably it is not possible to use it for selectively destroying/electroporating single cells independently of their type. De facto, as the position with respect to relatively large electrodes (and accordingly the field intensity to which they are subjected) is remarkably varying, such method can not operate in a homogeneous way on different cells.

The lysis is preferably induced using fields in a frequency range included between the cross-over frequency (beyond which cells change from negative (nDEP) to positive (pDEP) electrophoresis, and lower than the frequency beyond which the membrane potential results weakened due to the overcoming of the relaxation constant of the membrane.

Other documents of a recent publication, such as WO2005/075656 and US2005/0070018A1, relate to apparatus for electroporation of single cells based an the use of an array or a matrix of microelectrodes, on which cells are cultivated adherent (according to the international patent application) or equipped with conductive microwires for connecting cells to be electroporated to the electrodes and microfluidic channels for the cell displacement. Such apparatus do not give the possibility to organize the cells in a deterministic way, and the position of the cells with respect to the electrodes results aleatory. Therefore, the electric field to which they are subjected at the moment of electroporation results quite varying, so that the applied stimulus is sometimes statistically excessive (causing the death of the cell), or insufficient, lacking in the electroporation of the cell. The success percentage in the electroporation process then results sub-optimal and less effective.

SUMMARY OF THE INVENTION

An object of the present invention is to provide a method and an apparatus for operating on fluid samples containing particles, typically cells, for carrying out the transformation of one or more cells, which is free of limitations and/or drawbacks described for the known art.

In particular, an object of the present invention is to act on the control of the position of each particle existing in the sample, for the purpose of displacing such particles in a deterministic way, for operating in a selective way on each cell and/or performing in a more effective way operations such as electroporation.

Here and in the following, by terms "particles" or "particle", natural or artificial, micrometric or nanometeric entities are intended, such as cells, sub-cell components, viruses, liposomes, niosomes, microballs. Sometimes, the term cell will be used, but where not otherwise specified it should be intended as a non limiting example of the use for the detection and characterization of particles in the widest sense above described.

The present invention therefore relates to a method as specified in the claim 1.

In particular, non uniform, time varying force fields and integrated optical sensors are used. The force fields can be of positive or negative dielectrophoresis, electrophoresis or electro-hydrodynamic motions, characterized by a set of stable points of equilibrium for the particles (solid, liquid or gaseous).

In this way, restrictions of the known art are overcome by the present invention.

The implementation of the method according to the invention allows to transform cells in an effective and selective way, for example with the introduction of exogenous genetic material. Furthermore, it allows to accurately purify a sample of cells, possibly transformed, also from contaminants existing in a low percentage. Finally, it allows to quickly isolate a few cells of interest from a heterogeneous sample. The whole through the adoption of a single technology based on a same array of microelectrodes which are used both for moving cells within a micro-chamber, in which the array of electrodes is incorporated, and for producing the electroporation thereof.

Further features and advantages of the invention will result evident from the following description of some non limiting embodiments of the same, which is carried out with reference to the figures of the enclosed drawings.

DETAILED DESCRIPTION

Figure 1:
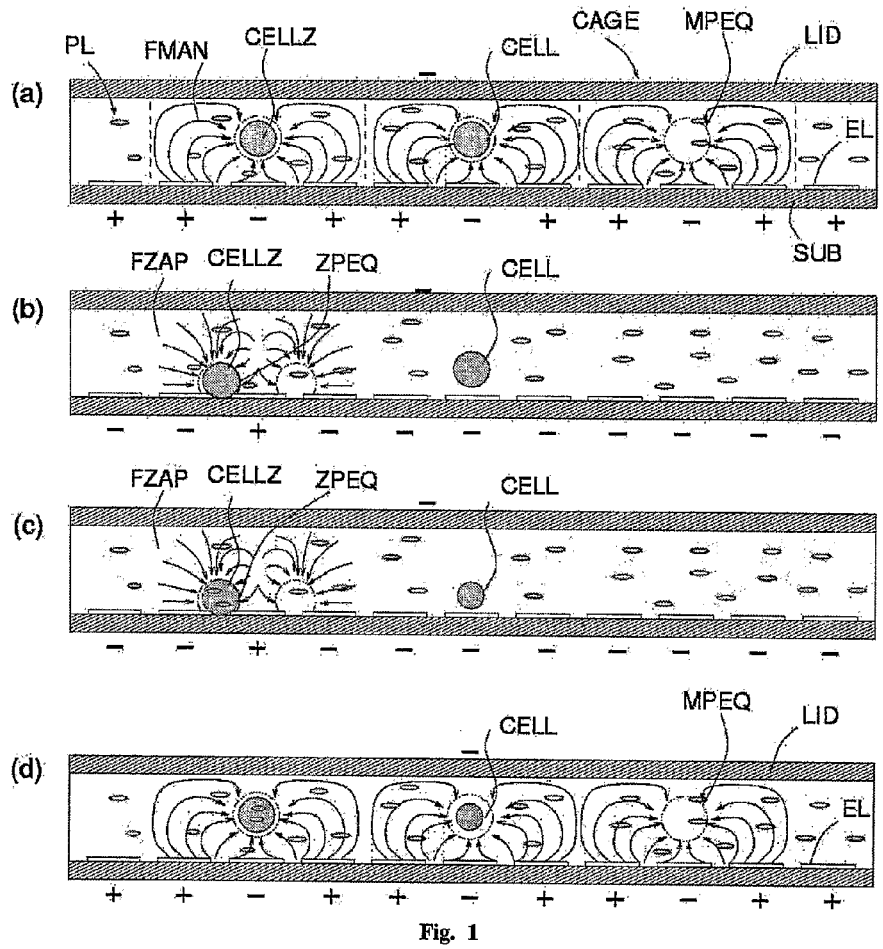
FIG. 1 diagrammatically shows the steps of the method according to the invention carried out in a manipulation apparatus shown in a sectional and elevation view.

The object of the present invention is to carry out a method for the manipulation and/or the transformation and/or the study of the optimal electroporation conditions and/or the detection of particles.

The method of the invention is based on the use of a non uniform force field (F) through which it attracts single particles or groups of particles (BEADS) towards positions of stable equilibrium (CAGE). Such field can be for example a negative (NDEP) or a positive (PDEP) dielectrophoresis field (DEP), an electrophoretic field (EF) or an electro-hydrodynamic (EHD) motions field.

The processing operated on cells is based on the application of localized electric fields capable of causing the temporary permeabilization of the cell membrane.

The method can also use integrated sensors, preferably of an optical and/or impedance meter type, for example in all those steps in which it is necessary to check the type of particles in proximity of certain electrodes. Alternatively, a similar information can be obtained through non-integrated optical sensors, coupled with a microscope which allows to examine the content of the micro-chamber.

Generation of Forces

There are different methods for the generation of forces for displacing particles, according to the known art, through arrays of electrodes (EL), carried on a substrate. Typically, according to preceding patent rights of the same Applicant (FIG. 1), a cover (LID) is used, which can be in turn an electrode, which delimits a micro-chamber within which particles (BEADS) are typically found in a liquid suspension. In case of dielectrophoresis (DEP), voltages applied are in phase periodic voltages (Vphip) shown by the addition symbol (+) and counter-phase periodic voltages (Vphin) shown by the subtraction symbol (−). By the term "counter-phase voltages", voltages out of phase of 180 degrees are Meant. The field generates a force which acts on the particles in a space region (CAGE), attracting them towards a point of equilibrium (PEQ). In case of negative DEP (NDEP), it is possible to generate closed force cages, according to the known art, if the cover (LID) is a conductive electrode; in this case, the point of equilibrium (PEQ) is established in correspondence with each electrode connected to Vphin (−) if the adjacent electrodes are connected to the opposite phase Vphip (+) and if the cover (LID) is connected with the phase Vphin (−). Such point of equilibrium (PEQ) is normally spaced apart in the liquid compared to the electrodes, whereby particles (BEADS) are, in a steady state, in levitation. In case of positive DEP (PDEP), the point of equilibrium (PEQ) is normally found in correspondence with the surface on which the electrodes are provided, and the particles (BEADS) are, in a steady state, contacting with the same. For the PDEP, the presence of further electrodes in the cover, (lid) is not necessary, because the points of equilibrium of the PDEP correspond to the maxima of the electric field. For the electro-hydrodynamic (EHD) motions, configurations of the electrodes generate some flows which drive the particles towards points of minimum of the flow.

In the following, for easiness, the use of closed negative dielectrophoresis cages as an execution force for the displacement of particles in the description of the methods of the invention is merely considered by way of non limiting example for the purposes of the present invention (for this reason, it is necessary to use a lid acting as an electrode). To those skilled in the art with ordinary skill, it is apparent how to generalize methods and apparatus described below for the use of different execution forces and different types of particles.

Electroporation Articles Assisted by Dielectrophoretic Manipulation

Particles are positioned in proximity of the gap between two electrodes by means of one of the execution forces above mentioned, for example by energizing the electrodes themselves with sinusoidal voltages of a first amplitude and frequency. The gap is preferably lower than 10 μm, and typically of the order of 1-2 μm, such that also a low voltage stimulus, compatible with the feed voltage of an integrated circuit (examples 2.5, 3.3 or 5 V) is sufficient to determine a trans-membrane potential capable of causing the reversible permeabilization of the particle.

This stimulus preferably consists of a sinusoidal impulse train of a second amplitude and a second frequency.

FIG. 1 shows in a sectional view the temporal evolution of force fields and voltage "patterns" (or the complex of configurations of (+) or (−) state of the electrodes) applied to the electrodes according to a preferred embodiment of the invention. In FIG. 1(a) cells (CELL) are in nDEP, in suspension in the liquid in a first point of equilibrium (MPEQ). In FIG. 1(b), the pattern of voltages applied to the electrodes (EL) changes, as well as the frequency and optionally the amplitude of the applied voltages, such that also the force to which the cells (CELL) are subjected changes in pDEP (FZAP). However, thanks to the change of voltage pattern only the cell to be electrophorated (CELLZ) is subjected to a significant force, therefore it is attracted towards a new stable point of equilibrium (ZPEQ). In proximity of such point, the electric field is the highest and the frequency is such that a trans-membrane potential sufficient to electroporate the cell is determined. In this way, at least a compound (PL) existing in suspension is able to penetrate within the cell.

Such compound can be a chemical compound (dye, drug, peptide) in solution in the fluid in which particles are dipped, or it could be, for example, a plasmide, etc. according to the known art, or second PL particles of desired type and quantity could be present in suspension within the fluid.

Figure 2:
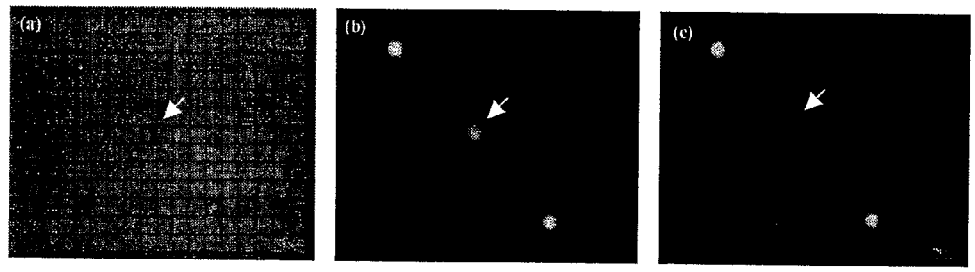
FIG. 2 shows with photographic sequences taken in a top plan view with respect to the apparatus of FIG. 1, the practical execution of the method of FIG. 1.

FIG. 2 shows the electroporation of a single cell. Cells, FIG. 2(a) are trapped in nDEP (frequency =50 kHz, peak-to-peak voltage to electrodes 3.3 V, peak-to-peak voltage to the lid 6.6 V). FIG. 2(b) shows the fluorescence imagine. The field is then mutated in pDEP (two 500 kHz impulses, amplitude of peak-to-peak voltage to electrodes 2 V, amplitude of peak-to-peak voltage to the lid 4 V), and the selected cell undergoes a pore opening which causes the release of calcein (previously loaded within cells, for the purpose of carrying out the experiment) and the fluorescence decrease (FIG. 2(c)).

With the optical-type integrated sensors with fluorescence detection (see previous patents of the same Applicant) the effective transformation can be checked, for example through the expression of Green Fluorescent Protein (GFP).

Method for the Optimization of Electro Oration Stimuli

Upon the array of electrodes cells can be placed and stimuli with different amplitude and/or frequency parameters can be tried on each of them or groups of them, in order to rapidly determine the more effective stimulus.

For example, the electroporation can be checked with integrated optical sensors, as above described, or with the monitoring of a possible introduction of a dye (dye or colouring matter) within the cell (for example Trypan blue), normally unable to penetrate the membrane.

Figure 3:
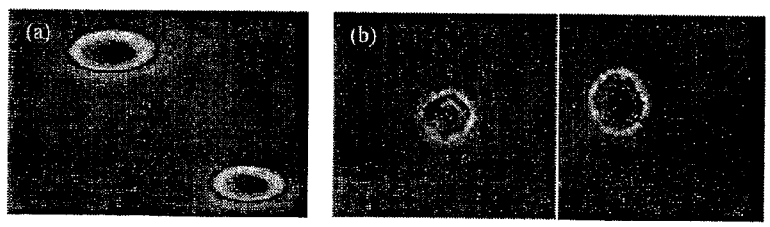
FIG. 3 shows with photographic sequences some cells before and after the electroporation.

FIG. 3 shows cells in Trypan blue before, FIG. 3(a) and after, FIG. 3(b), the electroporation according to the protocol above described. In FIG. 3(b), it can be noted that Trypan blue is penetrated within the cell. With integrated optical sensors the inlet of the dye can be detected as well as the occurrence of the electroporation.

Alternatively, the dispersion of a dye present within the cell caused by the diffusion of the dye outside at the pore opening can be controlled. For example, fluorescent calcein within the cell could be released outside and determine a decrease of the cell fluorescence, as above described.

The method foresees to iteratively apply stimuli of growing intensity on single cells, measure the number of electroporated cells for defining the dependence curve of the electroporation percentage as a function of the applied stimuli.

Method for the Adjustment of Electro Oration Stimuli for Each Cell

On the array of electrodes, cells can be positioned and stimuli of growing intensity can be tried thereon and the possible inlet of a dye normally unable to penetrate the membrane can be controlled with integrated optical sensors.

Based on what has been described, it is apparent that the invention allows to carry out the selection or the processing of first particles sensitive to the application of an external stimulus and provides the step of producing, through the application of such external stimulus, the permeabilization of at least one said first selected particle; in particular, it provides the steps of:

a) bringing first particles (CELL) in proximity of electrodes (EL) of an array of selectable electrodes having dimensions comparable or lower (i.e. smaller) than those of said particles, to which a first configuration (PMAN) of voltages is applicable for organizing said first particles (CELL) through a first force field (FMAN) by selectively energizing said electrodes (EL);

b) applying to said electrodes a second configuration (PZAP) of voltages, so as generate a second force field (FZAP), substantially positioned in proximity of at least one first selected particle to be permeabilized (CELL) and such to produce the application to said at least one first selected particle of a stimulus suitable for bringing said at least one first selected particle in a permeabilized state for at least a fraction of the length of said stimulus.

The method according to the invention further includes the step of:

c) contacting said at least one first selected particle in a permeabilized state with at least a second particle; wherein steps b) and c) are carried out so as to produce the penetration of said at least one second particle within said at least one first selected particle in a permeabilized state, as it is diagrammatically shown in FIG. 1.

First particles are dipped in a fluid and the step c) is carried out by dipping second particles within the fluid and extending said step b) for a time sufficient to allow that at least one said second particle penetrates within said at least one first selected particle, which is in a permeabilized state.

Alternatively, second particles are dipped in the fluid and then at least one selected said second particle is displaced towards said at least one first selected particle kept in a permeabilized state, preferably by applying to at least said selected second particle a force field (FMAN) obtained by selectively energizing the electrodes (EL) of the array of selectable electrodes applying to the electrodes a sequence of voltage configurations properly selected.

The stimulus applied by the field can be such to maintain the selected first particles in a permeabilized state for a predetermined time also after the removal of the stimulus itself; step c) can therefore be carried out by dipping second particles within the fluid in which first particles are dipped and by moving first particles in a permeabilized state towards second particles applying to the same a force field (FMAN) obtained by selectively energizing the electrodes (EL) of the array of selectable electrodes applying to the electrodes a sequence of pre-fixed voltage configurations.

Figure 4:
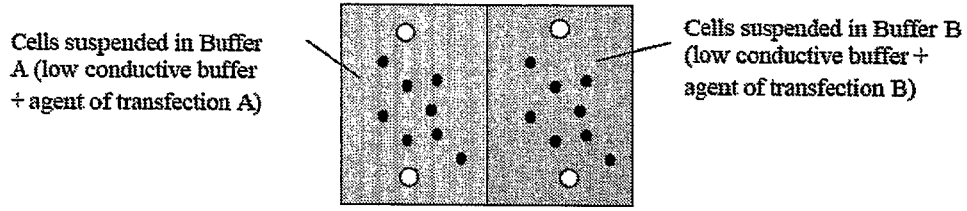
FIGS. 4, 5*a*, 5*b* diagrammatically show possible execution protocols of the method according to the invention.
Figure 5A:
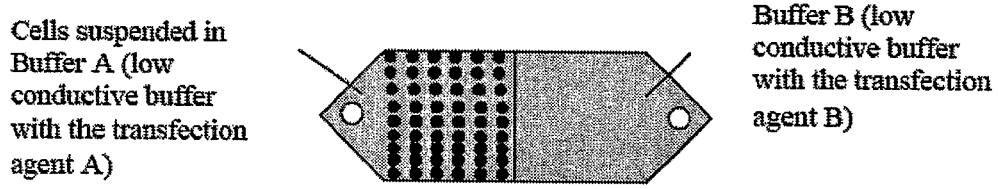
Figure 5B:
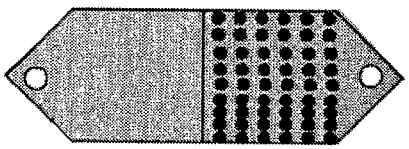

With reference to FIGS. 4, 5a, 5b first particles can be dipped in a first fluid, for example they can already be contained in suspension in the first fluid; and the step c) can be carried out by dipping second particles in a second fluid contiguous to the first fluid (in which second fluid, for example, second particles can already be dipped) and by displacing particles in a permeabilized state (electroporated) present in the first fluid, from the first fluid to the second one by applying to the particles a suitable force field (FMAN) energizing the electrodes by applying to the same electrodes a sequence of pre-fixed voltage configurations. Subsequently, first particles transformed for receiving within them second particles can be brought back in the first fluid, again applying a suitable configuration or sequence of voltage configurations to the electrodes.

When the first particles are dipped in a fluid, the method described can alternatively include the step of c) introducing within the fluid in which first particles are dipped at least a solution compound; and d) allowing said compound to penetrate within first particles which are in a permeabilized state (previously electroporated through the electrodes).

When first particles are dipped in a first fluid contained in a micro-chamber equipped with the array of electrodes, the method according to the invention (FIG. 4) includes the steps of:

c) introducing within the micro-chamber a second fluid by operating in a laminar motion such that the second fluid is not mixed with the first one (FIG. 5a);

d) introducing in the second fluid at least a dissolved compound (an operation that can obviously be carried out also before the introduction step of the second fluid in the micro-chamber, FIG. 5a);

e) displacing first particles in a permeabilized state from the first fluid to the second one by applying to the particles a force field (FMAN) obtained by selectively energizing said electrodes (EL) of said array of selectable electrodes by applying to said electrodes a sequence of pre-fixed voltage configurations (FIG. 5b);

f) allowing said compound to penetrate within selected first particles in a permeabilized state, subject to electroporation of such selected first particles, an operation which can take place while the first particles are dipped in the second liquid/fluid or, if the imparted stimulus is suitable for maintaining the first particles to which it is applied in a permeabilized state for a predetermined time also after the removal of the stimulus, while the first particles are still in the first fluid, in order to then displace them in the second fluid while they are still in a permeabilized state.

Generally speaking, the first particles can be dipped in a plurality of different fluids contained in a micro-chamber equipped with said array of electrodes and which have been introduced in said micro-chamber by operating in a laminar motion such that said different fluids do not mix together.

Preferably, as above described, the first particles are biological entities having a permeabilizable and lysable membrane, for example a cell, and, the stimulus consists of bringing the trans-membrane potential of the selected particles at such a value to produce the permeabilization of the membrane. The fluid in which, according to the invention, particles to be electroporated are dipped is always selected so as to present a relatively low electric conductivity, such that it is possible to pass to pDEP in order to attract cells in the maxima of the field, sufficient to cause such a trans-membrane potential to create pores.

Finally, according to a possible variant of the method of the invention, it provides to apply stimuli of a growing intensity to a plurality of said selected first particles and to measure, for each applied stimulus, the number of particles existing in a permeabilized state through sensors integrated with said array of electrodes, in a single chip. For example, first particles are dipped in a fluid and the fluid contains a compound suitable for being detected by the sensors at least when it penetrates within those said first particles which are in a permeabilized state.

Method for Adjusting a Priori Electro Oration Stimuli for Each Cell

Should information about the optimal value of stimuli, dependently on the cell characteristics, be available (for example following to characterizations as per the above methods), the following method can be adopted "a priori".

On the array of electrodes, it is possible to previously detect by the sensors (preferably optical and/or impedance meter sensors integrated within the chip) the characteristics of each cell to be electroporated, such as for example the dimensions, and to programme stimuli to be locally applied, so as to optimize, locally site by site, or electrode by electrode, the success percentage of the electroporation for each specific cell.

The invention claimed is:

1. Method for selecting and processing of first particles sensitive to the application of an external stimulus, comprising:
   a) selectively energizing electrodes (EL) of an array of selectable electrodes having dimensions identical with or smaller than those of said first particles to apply to all of said electrodes a first pattern (PMAN) of voltages to generate a first force field (FMAN) by which said first particles (CELL) are organized, bringing said first particles (CELL) towards first points of stable equilibrium (MPEQ) situated in proximity of said electrodes (EL); and
   b) applying to all and the same said selectable electrodes a second pattern (PZAP) of voltages, different from the first pattern (PMAN) to provide between at least two selected electrodes of said array adjacent to each other and positioned in proximity of at least one selected first particle to be permeabilized (CELL) a second force field (FZAP), to attract the at least one selected first particle to be permeabilized (CELL) to a second point of stable equilibrium (ZPEQ) positioned in a gap between the said at least two selected electrodes, and to simultaneously produce the application to said at least one selected first particle of a stimulus suitable for bringing said at least one selected first particle in a permeabilized state for a time, wherein said time is at least a fraction of the time length of said stimulus; said first and second pattern of voltages being applied in a time sequence to the same said electrodes.

2. Method according to claim 1, further comprising:
   c) contacting said at least one selected first particle in a permeabilized state with at least one second particle;
   wherein said steps b) and c) are carried out to produce the penetration of said at least one second particle within said at least one selected first particle in a permeabilized state.

3. Method according to claim 2, wherein said first particles are dipped in a fluid; and wherein said step c) is carried out with said at least one second particle also dipped in said fluid and extending said step b) for a time sufficient to allow said at least one second particle to penetrate within said at least one selected first particle, which is in a permeabilized state.

4. Method according to claim 2, characterized in that said first particles are dipped in a fluid; said step c) being carried out with said at least one second particle also dipped in said fluid and displacing at least one selected second particle towards said at least one selected first particle kept in a permeabilized state by applying to said at least selected second particle a force field (FMAN) obtained by selectively energizing said electrodes (EL) of said array of selectable electrodes applying to said electrodes a sequence of pre-fixed voltage configurations.

5. Method according to claim 2, wherein said stimulus is suitable for maintaining said at least one selected first particle in a permeabilized state for a pre-fixed time also after the removal of the stimulus, said first particles are dipped in a first fluid, said step c) is carried out with said at least one second particle also dipped in said first fluid, said step c) is carried out by displacing the at least one selected first particle in a permeabilized state towards said at least one second particle by applying to the at least one selected first particle a force field (FMAN), which force field is obtained by selectively energizing said electrodes (EL) of said array of selectable electrodes by applying to said electrodes a sequence of pre-fixed voltage configurations.

6. Method according to claim 2, characterized in that said first particles are dipped in a first fluid in step a); said step c) being carried out with said at least one second particle dipped in a second fluid contiguous to the first one; and further comprising the step of displacing said at least one selected first particle from the first fluid to the second one by applying to the at least one selected first particle a force field (FMAN) obtained by selectively energizing said electrodes (EL) of said array of selectable electrodes by applying to said electrodes a sequence of pre-fixed voltage configurations.

7. Method according to claim 6, characterized in that said steps b) and c) are carried out after displacing the at least one selected first particle to the second fluid or before displacing the at least one selected first particle to the second fluid provided that said stimulus is suitable for maintaining said at least one selected first particle in a permeabilized state for a pre-fixed time also after the removal of the stimulus and is sufficient to allow the displacement of the at least one selected first particle from the first fluid to the second fluid.

8. Method according to claim 2, further comprising checking if the penetration of said at least one second particle in said at least one selected first particle has occurred.

9. Method according to claim 8, wherein the said step of checking is carried out through sensors integrated with said array of selectable electrodes in a single chip.

10. Method according to claim 1, wherein said first particles are dipped in a fluid; said method further comprising the steps of
    c) having, in the fluid in which first particles are dipped, at least a compound in solution; and
    d) allowing said compound to penetrate within said at least one selected first particle in a permeabilized state.

11. Method according to claim 10, further comprising checking if the penetration of said compound in said at least one selected first particle has occurred.

12. Method according to claim 1, characterized in that said first particles are dipped in a first fluid contained in a micro-chamber equipped with said array of electrodes; said method further comprising the steps of:
    c) introducing in said micro-chamber a second fluid by operating in a laminar motion such that the second fluid is not mixed with the first one, the second fluid containing at least a dissolved compound;
    d) displacing said at least one selected first particle from the first fluid to the second one by applying to said at least one selected first particle a force field (FMAN) obtained by selectively energizing said electrodes (EL) of said array of selectable electrodes by applying to said electrodes a sequence of pre-fixed voltage configurations;
    e) allowing said compound to penetrate within said at least one selected first particle in a permeabilized state; said steps a) and b) being carried out when said at least one selected first particle is in the second fluid or, provided that said stimulus is suitable for maintaining said at least one selected first particle in a permeabilized state for a predetermined time also after the removal of the stimulus, and sufficient to allow the displacement from the first fluid to the second fluid, when said at least one selected first particle is within the first fluid.

13. Method according to claim 1, wherein said first particles are dipped in a plurality of different fluids contained in a micro-chamber equipped with said array of selectable electrodes and which have been introduced in said micro-chamber by operating in a laminar motion such that said different fluids do not mix together.

14. Method according to claim 1, wherein said first particles are biological entities having a permeabilizable and lysable membrane, wherein said stimulus consists of bringing the trans-membrane potential of said at least one selected first particle at a value to produce the permeabilization of the membrane.

15. Method according to claim 14, wherein said first particles are cells.

16. Method according to claim 1, further comprising checking if the permeabilization of said at least one selected first particle has occurred.

17. Method according to claim 16, wherein the said step of checking is carried out through sensors integrated with said array of selectable electrodes in a single chip.

18. Method according to claim 1, comprising the step of:
applying said external stimulus to a plurality of said first particles with a growing intensity; and
measuring, for each applied intensity, the number of first particles existing in a permeabilized state through sensors integrated with said array of selectable electrodes in a single chip.

19. Method according to claim 18, wherein said first particles are dipped in a fluid and said fluid contains a compound suitable for being detected by said sensors at least when it penetrates within those said first particles which are in a permeabilized state.

20. Method according to claim 1, wherein a value of said external stimulus to be applied to each one of a plurality of first particles to obtain an optimal permeabilization of the first particle is known a priori, the method further comprising:
collecting information about the optimal value of stimuli to be applied through said electrodes depending on known characteristics of the first particles;
detecting, through sensors said known characteristics for identifying selected first particles; and
programming said external stimulus to be locally applied to said selected first particles in such a manner to obtain said optimal permeabilization of each selected first particle.

21. Method according to claim 20, wherein the detecting is carried out through sensors integrated on chips carrying said array of selectable electrodes.

22. Method for selecting and processing of first particles sensitive to the application of an external stimulus, comprising:
a) selectively energizing electrodes (EL) of an array of selectable electrodes having dimensions identical with or smaller than those of said first particles to apply to all of said electrodes a first pattern (PMAN) of voltages to generate a first force field (FMAN) by which said first particles (CELL) are organized, bringing said first particles (CELL) in proximity of said electrodes (EL);
b) applying to all said selectable electrodes a second pattern (PZAP) of voltages, to provide between at least two selected electrodes of said array adjacent to each other and positioned in proximity of at least one selected first particle to be permeabilized (CELL) a second force field (FZAP), to produce the application to said at least one selected first particle of a stimulus suitable for bringing said at least one selected first particle in a permeabilized state for a time, wherein said time is at least a fraction of the time length of said stimulus; and
c) contacting said at least one selected first particle in a permeabilized state with at least one second particle;
said steps b) and c) being carried out so as to produce the penetration of said at least one second particle within said at least one selected first particle in a permeabilized state; and wherein:
said stimulus is suitable for maintaining said at least one selected first particles in a permeabilized state for a pre-fixed time also after the removal of the stimulus, wherein said first particles are dipped in a first fluid and said step c) is carried out with said at least one second particle also dipped in said first fluid and by displacing the at least one selected first particle in a permeabilized state towards said at least one second particle by applying to the at least one selected first particle a force field (FMAN), which force field is obtained by selectively energizing said electrodes (EL) of said array of selectable electrodes by applying to said electrodes a sequence of pre-fixed voltage configurations.

23. Method for selecting and processing of first particles sensitive to the application of an external stimulus, comprising:
a) selectively energizing electrodes (EL) of an array of selectable electrodes having dimensions identical with or smaller than those of said first particles to apply to all of said electrodes a first pattern (PMAN) of voltages to generate a first force field (FMAN) by which said first particles (CELL) are organized, bringing said first particles (CELL) in proximity of said electrodes (EL);
b) applying to all said selectable electrodes a second pattern (PZAP) of voltages, to provide between at least two selected electrodes of said array adjacent to each other and positioned in proximity of at least one selected first particle to be permeabilized (CELL) a second force field (FZAP), to produce the application to said at least one selected first particle of a stimulus suitable for bringing said at least one selected first particle in a permeabilized state for a time, wherein said time is at least a fraction of the time length of said stimulus, wherein said first particles are dipped in a plurality of different fluids contained in a micro-chamber equipped with said array of selectable electrodes and which have been introduced in said micro-chamber by operating in a laminar motion such that said different fluids do not mix together.

* * * * *